United States Patent
Serizawa

(10) Patent No.: US 9,427,010 B2
(45) Date of Patent: Aug. 30, 2016

(54) CAROTENOID-CONTAINING COMPOSITION

(71) Applicant: FUJIFILM Corporation, Minato-ku, Tokyo (JP)

(72) Inventor: Shinichiro Serizawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 104 days.

(21) Appl. No.: 13/969,140

(22) Filed: Aug. 16, 2013

(65) Prior Publication Data

US 2013/0337136 A1 Dec. 19, 2013

Related U.S. Application Data

(63) Continuation of application No. PCT/JP2012/053187, filed on Feb. 10, 2012.

(30) Foreign Application Priority Data

Feb. 18, 2011 (JP) ................................. 2011-033812

(51) Int. Cl.
| | | |
|---|---|---|
| C11B 5/00 | (2006.01) |
| A23L 1/30 | (2006.01) |
| A23L 1/275 | (2006.01) |
| A23L 2/52 | (2006.01) |
| A23L 2/58 | (2006.01) |
| A61K 8/39 | (2006.01) |
| A61Q 19/00 | (2006.01) |
| C09B 61/00 | (2006.01) |
| A61K 8/31 | (2006.01) |
| A61K 8/36 | (2006.01) |
| A61K 8/365 | (2006.01) |
| A61K 8/49 | (2006.01) |

(52) U.S. Cl.
CPC ............ *A23L 1/3002* (2013.01); *A23L 1/2753* (2013.01); *A23L 2/52* (2013.01); *A23L 2/58* (2013.01); *A61K 8/31* (2013.01); *A61K 8/36* (2013.01); *A61K 8/365* (2013.01); *A61K 8/39* (2013.01); *A61K 8/498* (2013.01); *A61Q 19/00* (2013.01); *C09B 61/00* (2013.01); *A61K 2800/10* (2013.01)

(58) Field of Classification Search
CPC ......... A23L 1/2753; A23L 2/52; A23L 2/58; A23L 1/3002; A61K 8/31; A61K 8/36; A61K 8/365; A61K 8/39; A61K 8/498; A61K 2800/10; C09B 61/00; A61Q 19/00
USPC ................. 426/541, 545, 546, 601
See application file for complete search history.

(56) References Cited

U.S. PATENT DOCUMENTS

| | | | | |
|---|---|---|---|---|
| 5,863,953 | A | * | 1/1999 | Luddecke et al. ............ 514/691 |
| 2007/0286930 | A1 | | 12/2007 | Ogawa et al. |
| 2011/0275592 | A1 | | 11/2011 | Tanisaka |

FOREIGN PATENT DOCUMENTS

| | | |
|---|---|---|
| JP | 09-157159 A | 6/1997 |
| JP | 2000-106843 A | 4/2000 |
| JP | 2000106844 A | 4/2000 |
| JP | 2004-512294 A | 4/2004 |
| JP | 2008013751 A | 1/2008 |
| JP | 2008143841 A | 6/2008 |
| JP | 2009-114184 A | 5/2009 |
| JP | 2010-168285 A | 8/2010 |
| JP | 2011-241177 A | 12/2011 |
| WO | 2010084789 A1 | 7/2010 |

OTHER PUBLICATIONS

Notice of Reasons for Rejection, dated Oct. 28, 2014, issued in related JP Application 2012-027711, 5 pages in English and Japanese.
Notification of First Examination Opinion, dated Jun. 19, 2014, issued in corresponding CN Application No. 201280009270.8, 10 pages in English and Chinese.
International Search Report for PCT/JP2012/053187 dated Mar. 19, 2012, 5 pages in Japanese and English.
Written Opinion for PCT/JP2012/053187 dated Mar. 19, 2012, 21 pages in Japanese and English.
Office Action dated Feb. 2, 2015, issued by the State Intellectual Property Office of P.R. China in counterpart Chinese Application No. 201280009270.8.
Submission of Publications, submitted by third party on Dec. 9, 2014, received by Applicant on Jan. 13, 2015, for corresponding JP Application No. 2012-27711, 4 pages in English and Japanese.
Extended European Search Report (EESR) dated Dec. 11, 2015, issued by the European Patent Office in corresponding European Application No. 12746826.2.
Ogawa M: "Astaxanthins containing composition for foodstuffs, consists of natural extract containing astaxanthin and/or ester, oil-solubility emulsifier, water-soluble emulsifier and aqueous medium", WPI/Thomson, vol. 2008, No. 1, Oct. 18, 2007, XP-002744876, 2 pages total.

* cited by examiner

*Primary Examiner* — Leslie Wong
(74) *Attorney, Agent, or Firm* — Sughrue Mion, PLLC

(57) ABSTRACT

A carotenoid-containing composition, comprising: a carotenoid component comprising at least one crystalline carotenoid, at least 90% by mass of the crystalline carotenoid being non-crystalline; a (poly)glycerol fatty acid ester having from 1 to 6 glycerin units and from 1 to 6 fatty acid units and having at least one hydroxyl group from a glycerin unit; and at least one phenolic antioxidant selected from the group consisting of aromatic carboxylic acids, cinnamic acids, and ellagic acids.

13 Claims, No Drawings

CAROTENOID-CONTAINING COMPOSITION

CROSS-REFERENCE TO RELATED APPLICATIONS

This application is a continuation application of International Application No. PCT/JP2012/053187, filed Feb. 10, 2012, which is incorporated herein by reference. Further, this application claims priority from Japanese Patent Application No. 2011-033812, filed Feb. 18, 2011, which are incorporated herein by reference.

TECHNICAL FIELD

The present invention relates to carotenoid-containing compositions.

BACKGROUND ART

In recent years, various compositions containing carotenoids have been proposed by paying attention to the high functionalities of the carotenoids. Since a carotenoid is generally widely known as a poorly soluble ingredient, the form of an emulsified composition is typically adopted.

As an emulsified composition containing a carotenoid, for example, Japanese Patent Application Laid-Open (JP-A) No. 9-157159 discloses a carotenoid-containing composition that is prepared by emulsifying an oil phase, prepared by dissolving a carotenoid in an oil or fat to enhance absorbability of the carotenoid, into an aqueous phase containing a polyhydric alcohol in the presence of a polyglycerol fatty acid ester and lecithin, and has an average particle diameter of 100 nm or less in the above-described oil phase. Further, JP-A No. 2004-512294 discloses a composition in which a carotenoid having provitamin A activity, such as β-carotene, and a carotenoid having no provitamin A activity, such as lycopene, are combined to treat a symptom of aging.

On the other hand, JP-A No. 2010-168285 discloses an emulsion composition that contains a polyglycerol fatty acid ester and a nonionic emulsifier different from the polyglycerol fatty acid ester, such as a sucrose fatty acid ester, at a specified quantitative ratio as well as a high-melting-point carotenoid. JP-A No. 2010-168285 discloses that there can be provided an emulsion composition that contains a high-melting-point carotenoid and has excellent storage stability and high transparency by making such an emulsion composition.

Further, JP-A No. 2000-106843 discloses an anti-fading agent for a material containing a carotenoid-based pigment, containing the hydrolysate of defatted yolk and a water-soluble antioxidant as active components for the purpose of sufficiently preventing a carotenoid-based pigment from fading.

SUMMARY OF INVENTION

Technical Problem

Examples of carotenoids include carotenoids with high crystallinity such as lycopene, and crystals may be heated at high temperature and dissolved and may be used as non-crystalline components when such crystalline carotenoids are prepared as oil components.

However, decomposition or disappearance of a carotenoid may occur due to high-temperature treatment in order to achieve a non-crystalline state. Further, decomposition or disappearance of a carotenoid is known to proceed over time since carotenoids are unstable substances.

Therefore, the present invention provides a carotenoid-containing composition that can stably contain a crystalline carotenoid in a non-crystalline state.

Solution to Problem

The present invention provides each aspect described below.

[1] A carotenoid-containing composition including: a carotenoid component comprising at least one crystalline carotenoid, at least 90% by mass of the crystalline carotenoid being non-crystalline; a (poly)glycerol fatty acid ester having from 1 to 6 glycerin units and from 1 to 6 fatty acid units and having at least one hydroxyl group from a glycerin unit; and at least one phenolic antioxidant selected from the group consisting of aromatic carboxylic acids, cinnamic acids, and ellagic acids.

[2] The carotenoid-containing composition according to [1], in which the crystalline carotenoid is lycopene.

[3] The carotenoid-containing composition according to [1] or [2], in which the phenolic antioxidant is a cinnamon acid.

[4] The carotenoid-containing composition according to any of [1] to [3], in which the phenolic antioxidant is a cinnamon acid; and the cinnamon acid is at least one selected from the group consisting of ferulic acid, γ-orizanol, caffeic acid and chlorogenic acid.

[5] The carotenoid-containing composition according to any of [1] to [4], further including an ascorbic acid-based antioxidant as another antioxidant.

[6] The carotenoid-containing composition according to any of [1] to [5], in which the molecular weight of the (poly)glycerol fatty acid ester is 10000 or less.

[7] The carotenoid-containing composition according to any of [1] to [6], in which the total mass of the (poly)glycerol fatty acid ester is from 0.01 times to 10 times the total mass of the crystalline carotenoid.

[8] The carotenoid-containing composition according to any of [1] to [7], in which the content of the phenolic antioxidant in the composition is from 1.3 times to 15.0 times the content of the carotenoid component by molar ratio.

[9] The carotenoid-containing composition according to any of [5] to [8], further including an ascorbic acid-based antioxidant as another antioxidant, in which the content of the ascorbic acid-based antioxidant in the composition is from 0.6 times to 7.0 times the content of the carotenoid component by molar ratio.

[10] The carotenoid-containing composition according to any of [1] to [9], in which each fatty acid of the fatty acid units of the (poly)glycerol fatty acid ester is a fatty acid having a carbon number of from 8 to 22.

[11] A method for producing the carotenoid-containing composition according to any of [1] to [10], including: preparing an oil phase component mixed liquid including the carotenoid component, the (poly)glycerol fatty acid ester and the phenolic antioxidant; and heating the oil phase component mixed liquid under a condition of a temperature of not less than a dissolution temperature of the carotenoid component.

[12] The production method according to [11], wherein a difference between a maximum temperature during the heating and the dissolution temperature of the carotenoid component is 15° C. or less.

[13] The production method according to [11] or [12], further including mixing an oil phase composition obtained from an oil phase component heating process with an aqueous phase composition including an aqueous phase component and performing emulsification.

Advantageous Effects of Invention

In accordance with the present invention, a carotenoid-containing composition that can stably contain a crystalline carotenoid in a non-crystalline state can be provided.

DESCRIPTION OF EMBODIMENTS

The carotenoid-containing composition of the present invention is a carotenoid-containing composition including: a carotenoid component comprising at least one crystalline carotenoid, at least 90% by mass of the crystalline carotenoid being non-crystalline; a (poly)glycerol fatty acid ester having from 1 to 6 glycerin units and from 1 to 6 fatty acid units and having at least one hydroxyl group from a glycerin unit; and at least one phenolic antioxidant selected from the group consisting of aromatic carboxylic acids, cinnamic acids, and ellagic acids.

In accordance with the present invention, a carotenoid-containing composition can be provided that contains a crystalline carotenoid in a non-crystalline state and is capable of effectively suppressing the decomposition or disappearance of a carotenoid even during and after the preparation of the composition since the composition includes a given (poly)glycerol fatty acid ester and a given phenolic antioxidant as well as a carotenoid component containing the crystalline carotenoid. As a result, the crystalline carotenoid in a non-crystalline state can be stably maintained in the composition.

A numerical value range indicated by using "to" as used herein refers to a range including the numerical values described before and after "to" as the minimum and maximum values, respectively.

In accordance with the present invention, when plural substances corresponding to each component are present in a composition, the amount of each component in the composition means the total amount of the plural substances present in the composition unless otherwise specified.

The term "process" as used herein encompasses not only an independent process but also a process, in which the anticipated effect of this process is achieved, even if the process is not able to be definitely distinguished from another process.

As used herein, the expression "(poly)glycerol fatty acid ester" includes all glycerol fatty acid esters including one glycerin unit and one fatty acid unit, a glycerol fatty acid ester including plural units of either thereof, and a glycerol fatty acid ester including plural units of both thereof, and is used in the case of using these glycerol fatty acid esters without distinction.

The present invention will be described below.

The carotenoid content composition of the present invention may be in any form if including: a carotenoid component comprising at least one crystalline carotenoid, at least 90% by mass of the crystalline carotenoid being non-crystalline; a (poly)glycerol fatty acid ester having from 1 to 6 glycerin units and from 1 to 6 fatty acid units and having at least one hydroxyl group from a glycerin unit; and at least one phenolic antioxidant selected from the group consisting of aromatic carboxylic acids, cinnamic acids, and ellagic acids. The possible form of the carotenoid-containing composition may be an oil phase composition constituted only by components that can constitute an oil phase (hereinafter also simply referred to as "oil phase component") or an oil-in-water emulsified composition obtained by emulsification-mixing of the oil phase composition with an aqueous phase composition constituted only by a component that is a given water-soluble component and can constitute an aqueous phase (hereinafter also simply referred to as "aqueous phase component").

[Carotenoid Component]

The carotenoid component in the carotenoid-containing composition of the present invention contains at least one crystalline carotenoid and at least 90% by mass of the crystalline carotenoid is present in a non-crystalline state in the composition.

Since the crystalline carotenoid contained in the carotenoid component is non-crystalline, an effect that might be degraded due to the presence of a crystal substance does not deteriorate and the absorbability of the carotenoid component into the body may be enhanced.

It can be confirmed using known means for detecting a crystal structure that the crystalline carotenoid is non-crystalline. Further, a crystalline carotenoid may be confirmed by a usual method, for which, for example, differential scanning calorimetric measurement (Differential scanning calorimetry: DSC), observation by a polarizing microscope, X-ray diffraction, and the like can be used. An inability to confirm detection of any crystal substance by these known technologies can demonstrate non-crystallinity. In particular, in accordance with the present invention, it is preferable to confirm non-crystallinity based on the presence of a DSC endothermic peak. Specifically, endothermic and exothermic temperatures are determined for an emulsion that has been freeze-dried to remove water or for a powder composition in a powder state in one cycle of temperature-rise to temperature-fall (15° C./min) in a temperature range of from 30° C. to 200° C. using DSC Q2000 (TA Instruments Japan Inc.), and the absence of any endothermic peak demonstrates a non-crystalline state.

Further, in the carotenoid component, at least from 90 to 100 by mass % of the crystalline carotenoid may be non-crystalline, and from 95 to 100% by mass is preferably non-crystalline, in view of dynamic absorbability. For example, the comparison of the endothermic quantity of an endothermic peak from a carotenoid crystal in the composition of the present invention measured by differential scanning calorimetric measurement (Differential scanning calorimetry: DSC) with the endothermic quantity of the endothermic peak of a carotenoid crystal sample enables confirmation that at least 90 mass % of the crystalline carotenoid contained in the carotenoid component is non-crystalline. A case in which less than 90% by mass of the crystalline carotenoid is non-crystalline is not preferred since, for example, the amount of a crystal substance is increased when the carotenoid-containing composition is prepared as an emulsion.

The comparison of the spectra of the composition of the present invention in X-ray diffraction with the spectra of a carotenoid crystal sample also enables confirmation that at least 90% by mass of the crystalline carotenoid contained in the carotenoid component is non-crystalline.

Further, the content ratio of a crystalline carotenoid which is non-crystalline can be converted from a DSC peak area and results obtained from XRD (X-ray diffraction) using a carotenoid reagent which is a crystal substance that can be obtained as a commercially available product, based on the carotenoid reagent as 100%. Examples of the commercially available product of a carotenoid reagent that is a crystal substance include biochemical reagents available from Wako Pure Chemical Industries, Ltd.

As used herein, "crystalline carotenoid" does not refer to a specific carotenoid but means a carotenoid that may be present as a crystal substance at any temperature in a temperature range of from −5° C. to 35° C., in the case of the form of an oil, a paste, or the like containing the carotenoid, depending on various factors such as production methods, treatment and storage thereof. In particular, lycopene, β-carotene, δ-carotene, zeaxanthin, lutein, astaxanthin, fucoxanthin, and the like described below are highly effective when applied to the present invention as these are carotenoids in which crystal substances can easily be present.

Crystalline carotenoids are pigments from terpenoids with yellow to red and examples thereof may include those derived from plants, algae and bacteria. Further, the crystalline carotenoids are not limited to those derived from natural sources but may be any crystalline carotenoids as long as the crystalline carotenoids are obtained according to usual methods. Further, a crystalline carotenoid may be confirmed by a usual method, for which, for example, differential scanning calorimetric measurement (Differential scanning calorimetry: DSC), observation by a polarizing microscope, X-ray diffraction, and the like can be used.

Specific examples of the crystalline carotenoid according to the present invention include lycopene, α-carotene, β-carotene, γ-carotene, δ-carotene, actinioerythrol, bixin, canthaxanthin, capsorubin, β-8'-apo-carotenal (apocarotenal), β-12'-apo-carotenal, xanthophylls (e.g., astaxanthin, fucoxanthin, lutein, zeaxanthin, capsanthin, β-cryptoxanthin, violaxanthin, etc.), fucoxanthin, and hydroxyl or carboxyl derivatives thereof. Such crystalline carotenoids may be used alone or in combination of two or more kinds.

Lycopene is preferred as the crystalline carotenoids which can be used alone or in combination.

Especially, lycopene is preferred as a crystalline carotenoid since lycopene is kwon to have a very high antioxidant effect, a very high whitening effect, and the like and the addition of lycopene to food products, cosmetics, pharmaceutical raw materials, processed products thereof, and the like has been conventionally demanded, examined, and practiced.

Lycopene (sometimes called "rikopen (lycopene)") is a carotenoid having chemical formula $C_{40}H_{56}$ (molecular weight of 536.87) and belongs to carotenes that is one of the carotenoids. Lycopene is a red pigment having an absorption maximum at 474 nm (acetone).

Lycopene may be present in the form of cis- or trans-isomers with respect to conjugated double bonds at the center of the molecule, and examples include an all-trans form, a 9-cis form, a 13-cis form, and the like, any of which may be available in the present invention.

The carotenoid-containing composition of the present invention may also contain lycopene as a lycopene-containing oil or a lycopene-containing paste, which is separated or extracted from a natural product containing lycopene.

In nature, lycopene is contained in tomato, persimmon, watermelon, and pink grapefruit, and the above-described lycopene-containing oil may also be separated or extracted from these natural products.

Lycopene used in the present invention may also be an extract extracted from the natural products, an appropriately purified substance from the extract as needed, or a synthetic product.

In the present invention, lycopene extracted from tomato is particularly preferred in view of quality and productivity.

Further, in accordance with the present invention, a tomato extract, which is widely commercially available, may be used as the lycopene-containing oil or paste. Examples of such a lycopene-containing oil or paste include Lyc-O-Mato 15% and Lyc-O-Mato 6%, commercially available from Sunbright Co., Ltd.; LYCOPENE 18 commercially available from Kyowa Hakko Kogyo Co., Ltd.; and the like.

The crystalline carotenoid may singly constitute the carotenoid component or the crystalline carotenoid and an oil component (oil) used in extraction from a natural product may constitute the carotenoid component.

The content of the crystalline carotenoid in the composition is preferably from 0.1% by mass to 5% by mass, more preferably from 0.2% by mass to 4% by mass, further preferably from 0.3% by mass to 3% by mass, with respect to a total mass of the solid contents (all components excluding water) in the carotenoid-containing composition. In this range, still more improvement in effect by the crystalline carotenoid can be expected.

The carotenoid component may also contain a naturally-derived non-crystalline carotenoid (non-crystalline carotenoid) other than the above-described crystalline carotenoids.

[(Poly)glycerol Fatty Acid Ester]

The (poly)glycerol fatty acid ester in the carotenoid-containing composition of the present invention is a (poly) glycerol fatty acid ester having from 1 to 6 glycerin units and from 1 to 6 fatty acid units and having at least one hydroxyl group from a glycerin unit.

This specific (poly)glycerol fatty acid ester exhibits high compatibility with a crystalline carotenoid and reduces a dissolution temperature (melting point as defined later) of the crystalline carotenoid. Further, in a co-dissolved material of (poly)glycerol fatty acid ester and the crystalline carotenoid, recrystallization of the crystalline carotenoid is suppressed.

A (poly)glycerol fatty acid ester having 7 or more glycerin units has enhanced hydrophilicity and a lower affinity with a carotenoid while a carotenoid crystal suppressing effect cannot be expected in a (poly)glycerol fatty acid ester in which the number of a glycerin units is 7 or more. Further, since the crystallization of a carotenoid cannot be sufficiently suppressed in a (poly)glycerol fatty acid ester containing no hydroxyl group from a glycerin unit, such as a medium-chain triglyceride, the carotenoid crystal suppressing effect cannot be expected in a case in which the given amount of a hydroxyl group is not present.

The (poly)glycerol fatty acid ester is preferably an ester of glycerin with the number of glycerin units (average degree of polymerization) of from 1 to 6, more preferably from 1 to 4, with a fatty acid with the number of fatty acid units of from 1 to 6, more preferably from 1 to 5, and the number of carbon atoms of from 8 to 22 (e.g., caprylic acid, capric acid, lauric acid, myristic acid, palmitic acid, stearic acid, oleic acid, linoleic acid, and behenic acid), more preferably a fatty acid having from 14 to 18 carbon atoms, from the viewpoint of, e.g., the suppression of recrystallization.

In these (poly)glycerol fatty acid esters, a molecular weight is preferably 10000 or less, more preferably 3000 or less, further preferably 2500 or less, from the viewpoint of homogeneous solubility during co-dissolution. Further, the HLB of the (poly)glycerol fatty acid ester is preferably 9 or less, more preferably 6 or less, from the viewpoint of an affinity with a carotenoid.

Further, in a case in which the carotenoid-containing composition is a powder composition, a (poly)glycerol fatty acid ester that is solid at ordinary temperature is preferred from the viewpoint of the concentration of a carotenoid in the carotenoid powder composition and yield during hot-air drying in the production of the composition. That is, increase in the amount of an encapsulating agent is not needed and the sufficient amount of the carotenoid can be contained in the case of being solid at ordinary temperature. Further, the (poly)glycerol fatty acid ester that is solid at ordinary temperature is difficult to adhere to a contact surface during hot-air drying and reduction in the yield of the carotenoid powder composition can be suppressed.

Examples of such a (poly)glycerol fatty acid ester that is solid at ordinary temperature may include those in which a fatty acid constituting a fatty acid unit is a fatty acid having neither branched chain nor unsaturated bond and may include, e.g., glyceryl myristate, glyceryl monostearate, glyceryl distearate, diglyceryl monostearate, tetraglyceryl monostearate, tetraglyceryl tristearate, tetraglyceryl pentastearate, hexaglyceryl monostearate, hexaglyceryl tristearate, hexaglyceryl tetrabehenate, hexaglyceryl pentastearate, and the like.

Examples of (poly)glycerol fatty acid esters that can be used in the carotenoid-containing composition of the present invention include glyceryl myristate, glyceryl monostearate, diglyceryl monostearate, triglyceryl monostearate, hexaglyceryl pentastearate, triglyceryl dipalmitate, glyceryl distearate, tetraglyceryl tristearate, tetraglyceryl pentastearate, hexaglyceryl monostearate, hexaglyceryl tristearate, hexaglyceryl tetrabehenate, and the like, and glyceryl myristate, glyceryl monostearate, diglyceryl monostearate, tetraglyceryl pentastearate, or hexaglyceryl pentastearate is e preferred from the viewpoint of the suppression of recrystallization and homogeneous solubility.

The (poly)glycerol fatty acid esters that can be used in the carotenoid-containing composition may be used singly or in combination of two or more kinds.

The content (mass) of a (poly)glycerol fatty acid ester, depending on the kind or content of a crystalline carotenoid that is used, is preferably from 0.01 times to 10 times, more preferably from 0.1 times to 8 times, further preferably from 0.3 times to 5 times, the total mass of the crystalline carotenoid, from the viewpoint of the stability of the carotenoid-containing composition. A sufficient crystal suppressing effect can be expected when the total mass of the polyglycerol fatty acid ester in the carotenoid-containing composition is 0.01 times or more the total mass of the crystalline carotenoid, while increase in the particle diameters of dispersed particles in an emulsion (emulsified particles) can be suppressed in the case of 10 times or less.

[Phenolic Antioxidant]

The phenolic antioxidant in the carotenoid-containing composition of the present invention is at least one selected from the group consisting of aromatic carboxylic acids, cinnamic acids, and ellagic acids.

Each of these phenolic antioxidants has one phenolic hydroxyl group in the molecule, may suppress the decomposition or disappearance of the crystalline carotenoid during heat treatment for dissolving the crystal of the crystalline carotenoid, and enables the crystalline carotenoid to be highly efficiently utilized.

Examples of the aromatic carboxylic acids may include gallic acid (3,4,5-hydroxybenzoic acid) and derivatives thereof. Examples of the derivatives of gallic acid (3,4,5-hydroxybenzoic acid) may include gallic acid esters such as propyl gallate, epicatechin gallate, and epigallocatechin gallate; gallic acid glucosides such as gallotannin; and the like.

Examples of the cinnamic acids may include ferulic acid, chlorogenic acid, and the like, and derivatives thereof. Examples of the derivatives of ferulic acid and chlorogenic acid may include ferulic acid esters. Specific examples may include ferulic acid, γ-orizanol (rice bran extract), caffeic acid (coffeic acid or 3,4-dihydroxycinnamic acid), chlorogenic acid, glyceryl ferulate, dihydroferulic acid, and the like.

Examples of the ellagic acids may include ellagic acid.

The above-described phenolic antioxidants may be used singly or in combination of two or more kinds.

Further, the phenolic antioxidant preferably has a lower molecular weight, e.g., of preferably from 100 to 3000, more preferably from 100 to 1000, from the viewpoint of the stability of the carotenoid component.

The phenolic antioxidants are preferably cinnamic acids from the viewpoint of the stability of the carotenoid component, especially more preferably ferulic acid or γ-orizanol each of which is obtained as a rice bran extract, or a mixture thereof.

The total content of the phenolic antioxidant in the composition may be an amount effective for suppressing the decomposition or disappearance of the carotenoid component and may be from 1.3 times to 15.0 times the content of the carotenoid component by molar ratio, preferably from 2 times to 10 times, more preferably from 3 times to 8 times. The effect of suppressing the deterioration of the decomposition or disappearance of the carotenoid component is sufficiently exhibited when the total content of the phenolic antioxidant is 1.3 times or more the content of the carotenoid component by molar ratio, while the blending of the sufficient amount of the carotenoid component is not deteriorated in the case of 15.0 times or less.

Further, the carotenoid-containing composition of the present invention preferably contains another antioxidant as well as the phenolic antioxidant.

Examples of such an antioxidant may include ascorbic acid compounds. Examples of the ascorbic acid compounds include at least one selected from ascorbic acid, ascorbic acid esters, and salts thereof (hereinafter may be referred to as "ascorbic acid-based antioxidant"). It is supposed that the ascorbic acid-based antioxidant acts as a protective agent for a carotenoid component during high-temperature treatment. By using such an antioxidant together with a phenolic antioxidant, decomposition due to the heating of a carotenoid component (e.g., oxidative decomposition or the like) may be surely suppressed to suppress the decrease of the carotenoid component in the process of producing the carotenoid-containing composition.

Examples of the ascorbic acid-based antioxidant include L-ascorbic acid, sodium L-ascorbate, potassium L-ascorbate, calcium L-ascorbate, L-ascorbyl phosphate, magnesium salt of L-ascorbyl phosphate, L-ascorbyl sulfate, disodium salts of L-ascorbyl sulfate, L-ascorbyl stearate, L-ascorbyl 2-glycoside, L-ascorbyl palmitate, and L-ascorbyl tetraisopalmitate and the like; and ascorbic fatty acid esters such as L-ascorbyl stearate, L-ascorbyl tetraisopalmitate and L-ascorbyl palmitate. Among these, L-ascorbic acid, sodium L-ascorbate, calcium L-ascorbate, L-ascorbyl stearate, L-ascorbyl 2-glycoside, L-ascorbyl palmitate, magnesium salt of L-ascorbyl phosphate, disodium salts of L-ascorbyl sulfate and L-ascorbyl tetraisopalmitate is especially preferred from the viewpoint of reduction in temperature loss of carotenoid.

These ascorbic acid-based antioxidants may be contained as a single substance in the carotenoid-containing composition as an oil phase composition or may be blended with the carotenoid-containing composition as an oil phase composition in the form of an aqueous solution. The concentration of such an ascorbic acid-based antioxidant in an aqueous solution is, without particular limitation, generally preferably from 0.05% by mass to 5% by mass based on the total mass of the carotenoid-containing composition from the viewpoint of antioxidation.

Further, the total content of the ascorbic acid-based antioxidant in the composition is preferably from 0.6 times to 7.0 times, more preferably from 1.0 time to 5.5 times, further preferably from 2.0 times to 4.0 times the content of the carotenoid component by molar ratio, from the viewpoint of the suppression of the loss of the carotenoid component due to heat. The effect of suppressing the deterioration of the decomposition or disappearance of the carotenoid component is sufficiently exhibited when the total content of the ascorbic acid-based antioxidant is 0.6 times or more the content of the carotenoid component by molar ratio, while the blending of the sufficient amount of the carotenoid component is not deteriorated in the case of 7.0 times or less.

The carotenoid-containing composition may also contain BHT (butylated hydroxytoluene), BHA (butylated hydroxyanisole), or the like as an antioxidant other than the above.

From the viewpoint of the stability of a crystalline carotenoid in a non-crystalline state and the suppression of recrystallization, the carotenoid-containing composition of the present invention preferably has any of the following embodiments:

(1) a carotenoid-containing composition including: a carotenoid component comprising lycopene of which at least 90% by mass is present in a non-crystalline state; a (poly)glycerol fatty acid ester having from 1 to 6 glycerin units and from 1 to 6 fatty acid units and having at least one hydroxyl group from a glycerin unit; and at least one phenolic antioxidant selected from the group consisting of aromatic carboxylic acids, cinnamic acids, and ellagic acids, wherein a fatty acid of each fatty acid unit contained in the (poly)glycerol fatty acid ester is a fatty acid having from 8 to 22 carbon atoms; and the content of the phenolic antioxidant is from 2 times to 10 times the content of lycopene by molar ratio;

(2) a carotenoid-containing composition including: a carotenoid component comprising lycopene of which at least 90% by mass is in a non-crystalline state; a (poly)glycerol fatty acid ester having from 1 to 6 glycerin units and from 1 to 6 fatty acid units and has at least one hydroxyl group from a glycerin unit; and at least one phenolic antioxidant selected from the group consisting of aromatic carboxylic acids, cinnamic acids, and ellagic acids, wherein a fatty acid of each fatty acid unit contained in the (poly)glycerol fatty acid ester is a fatty acid having neither a branched chain nor an unsaturated bond and having from 8 to 22 carbon atoms; and the content of the phenolic antioxidant is from 1.5 times to 15 times the content of lycopene by molar ratio; and (3) a carotenoid-containing composition including: a carotenoid component comprising lycopene of which at least 90% by mass is in a non-crystalline state; a (poly)glycerol fatty acid ester having from 1 to 6 glycerin units and from 1 to 6 fatty acid units and having at least one hydroxyl group from a glycerin unit; at least one phenolic antioxidant selected from the group consisting of aromatic carboxylic acids, cinnamic acids, and ellagic acids; and an ascorbic acid-based antioxidant which is at least one selected from ascorbic acid and ascorbic acid esters, wherein a fatty acid of each fatty acid unit contained in the (poly)glycerol fatty acid ester is a fatty acid having from 8 to 22 carbon atoms; the content of the phenolic antioxidant is from 1.5 times to 15 times the content of lycopene by molar ratio; and the content of the ascorbic acid-based antioxidant is from 0.6 times to 7.0 times the content of lycopene by molar ratio.

In each of embodiments (1) to (3) described above, the phenolic antioxidant is further preferably a cinnamic acid.

In each of embodiments (1) to (3) described above, the content of the (poly)glycerol fatty acid ester is further preferably from 0.01 times to 10 times the total mass of the crystalline carotenoid.

In each of embodiments (1) to (3) described above, the (poly)glycerol fatty acid ester is further preferably at least one selected from the group consisting of glyceryl myristate, glyceryl monostearate, diglyceryl monostearate, triglyceryl monostearate, hexaglyceryl pentastearate, triglyceryl dipalmitate, glyceryl distearate, tetraglyceryl tristearate, tetraglyceryl pentastearate, hexaglyceryl monostearate, hexaglyceryl tristearate, and hexaglyceryl tetrabehenate.

Two or more of the further preferred of embodiments (1) to (3) described above may also be further combined.

[Other Components]

The carotenoid-containing composition may contain another oil component typically used as an oil phase component in addition to each component described above.

As such another oil component, which is not particularly limited as long as the component is not dissolved in an aqueous medium but is dissolved in an oil medium, the component having physical properties and functionality depending on the purpose may be appropriately selected and used, and, for example, unsaturated fatty acids, oils or fats such as coconut oils, fat-soluble vitamins such as tocopherol, and ubiquinones are preferably used.

Examples of unsaturated fatty acids include monovalent highly unsaturated fatty acids having at least 10 carbon atoms and preferably from 18 to 30 carbon atoms (ω-9, oleic acid, etc.) and polyvalent highly unsaturated fatty acids having at least 10 carbon atoms and preferably from 18 to 30 carbon atoms (ω-3, ω-6). Such unsaturated fatty acids may be any of known unsaturated fatty acids, and examples of ω-3 oils or fats may include linolenic acid, eicosapentaenoic acid (EPA) and docosahexaenoic acid (DHA) as well as fish oils containing these acids, and the like.

Examples of the ubiquinones include coenzymes Q such as coenzyme Q10; and the like.

Examples of the fat-soluble vitamins may include fat-soluble vitamins E, vitamins A, vitamins D, and oil-soluble derivatives of erythorbic acid, and, of these, fat-soluble vitamins E, which have high antioxidant functions and can also be used as radical scavengers (antioxidants), are preferred.

Examples of vitamins E include, but are not limited to, those selected from the compound group consisting of tocopherol and derivatives thereof and the compound group consisting of tocotrienol and derivatives thereof. They may be used alone or in combination of plural kinds. Also, vitamins E selected from the compound group consisting of tocopherol and derivatives thereof and the compound group consisting of tocotrienol and the derivatives thereof may be used in combination.

Examples of the compound group consisting of tocopherol and derivatives thereof include dl-α-tocopherol, dl-β-tocopherol, dl-γ-tocopherol, dl-δ-tocopherol, dl-α-tocopherol acetate, dl-α-tocopherol nicotinate, dl-α-tocopherol linoleate, dl-α-tocopherol succinate, and the like. Of these, dl-α-tocopherol, dl-β-tocopherol, dl-γ-tocopherol, dl-δ-tocopherol, and mixtures thereof (mixed tocopherols) are more preferred. Further, as the tocopherol derivatives, carboxylic acid esters thereof, particularly acetic acid esters, are preferably used.

Examples of the compound group consisting of tocotrienol and derivatives thereof include α-tocotrienol, β-tocotrienol, γ-tocotrienol, δ-tocotrienol, and the like. Further, as the tocotrienol derivatives, acetic acid esters thereof are preferably used.

Examples of vitamins A may include retinol, 3-hydroretinol, retinal, 3-hydroretinal, retinoic acid, 3-dehydroretinoic acid, vitamin A acetate, and the like. Examples of vitamins D may include vitamins D such as vitamins $D_2$ to $D_7$. Further, examples of other fat-soluble vitamin substances may include esters such as vitamin E nicotinate; and vitamins K such as vitamins $K_1$ to $K_3$.

Examples of fat-soluble vitamins may also include fatty acid esters of erythorbic acid, such as erythorbyl palmitate and erythorbyl tetraisopalmitate; fatty acid esters of vitamin $B_6$, such as pyridoxine dipalmitate, pyridoxine tripalmitate, pyridoxine dilaurate, and pyridoxine dioctanoate; and the like.

Examples of oils or fats other than the above include oils or fats (fatty oils) which are liquid and oils or fats (fats) which are solid, at ordinary temperature.

Examples of the liquid oils or fats include olive oil, camellia oil, macadamia nut oil, castor oil, avocado oil, evening primrose oil, turtle oil, corn oil, mink oil, rapeseed oil, egg yolk oil, sesame oil, persic oil, wheat germ oil, sasanqua oil, linseed oil, safflower oil, cotton seed oil, perilla oil, soybean oil, peanut oil, tea seed oil, kaya oil, rice bran oil, china wood oil, Japan tung oil, jojoba oil, germ oil, triglycerol, glycerol trioctanoate, glycerol triisopalmitate, salad oil, safflower oil (*Carthamus tinctorius* oil), palm oil, coconut oil, peanut oil, almond oil, hazelnut oil, walnut oil, grape seed oil, squalene, squalane, and the like.

Further, the solid oils or fats include beef tallow, hydrogenated beef tallow, neat's foot oil, beef bone fat, mink oil, egg yolk oil, lard, horse fat, mutton tallow, hydrogenated oil, cacao oil, coconut oil, hydrogenated coconut oil, palm oil, palm hydrogenated oil, *Rhus succedanea* fruit wax, *Rhus succedanea* kernel oil, hydrogenated castor oil, and the like.

Among the above, coconut oil which is a medium chain triglyceride is preferably used from the viewpoint of the particle diameter and stability of the emulsion composition.

In order to improve properties in the composition, it is preferred for the oil component in the present invention to contain a compound selected from the group consisting of tocopherol, tocotrienol, and derivatives thereof included in fat-soluble vitamins (hereinafter, the compound is referred to as "tocopherols", when appropriate) together with other oil phase component(s).

The tocopherol may be preferably combined in a range of from 5% by mass to 35% by mass, more preferably from 7% by mass to 20% by mass, with respect to the total mass of the oil component.

[Oil-in-Water Emulsified Composition]

As mentioned above, the carotenoid-containing composition of the present invention may be an oil-in-water emulsified composition obtained by emulsification-mixing with an aqueous phase composition or a powder composition obtained by drying the oil-in-water emulsified composition.

In this case, the content of the oil phase composition is preferably from 0.1% by mass to 50% by mass, more preferably from 0.5% by mass to 25% by mass, further preferably from 0.2% by mass to 10% by mass, in the case of the emulsified composition, from the viewpoint of exhibiting the function of an oil component. Further, in the case of the powder composition, the content is preferably from 10% by mass to 50% by mass, more preferably from 10% by mass to 40% by mass, further preferably from 10% by mass to 30% by mass, with respect to the total mass of the composition.

In the case of the oil-in-water emulsified composition, an emulsifier that may be used as an oil phase component, as well as the above-described component may be contained. Examples of such an emulsifier that may be used as the oil phase component include emulsifiers described below, with HLB of 7 or less.

[Aqueous Phase Composition]

The aqueous phase composition is constituted by an aqueous medium, particularly water, and preferably contains at least an emulsifier.

The emulsifier may be any of anionic surfactants, cationic surfactants, ampholytic surfactants, and nonionic surfactants.

Further, the emulsifier preferably has HLB of 10 or more, further preferably 12 or more, from the viewpoint of an emulsifying capacity. When HLB is too low, the emulsifying capacity may become insufficient. In addition, an emulsifier with HLB=5 or more and less than 10 may be combined from the viewpoint of a foam suppressing effect.

As used herein, HLB indicates hydrophilicity-hydrophobicity balance typically used in the field of surfactants and can be calculated using a generally used calculation equation such as Kawakami equation. Kawakami equation is described below.

$$HLB=7+11.7 \log(M_w/M_o)$$

wherein $M_w$ represents the molecular weight of a hydrophilic group(s); and $M_o$ represents the molecular weight of a hydrophobic group(s).

HLB values described in a catalog or the like may also be used.

As is clear from the above-described equation, an emulsifier having an arbitrary HLB value can be obtained utilizing the additivity of HLB.

The content of the emulsifier in the oil-in-water emulsified composition generally depends on the form of the composition and is preferably from 0.5 by mass to 30% by mass, more preferably from 1% by mass to 20% by mass, further preferably from 2% by mass to 15% by mass with respect to the total mass of the composition in the case of the emulsified composition or is preferably from 0.1% by mass to 50% by mass, more preferably from 5% by mass to 45% by mass, further preferably from 10% by mass to 30% by mass with respect to the total of the composition in the case of the powder composition. The content within the ranges is preferred in view of easily reducing the interfacial tension between an oil phase and a poor solvent phase, preventing an excessive amount, and inhibiting the occurrence of a problem such as the poor foaming of the emulsified composition.

Further, the emulsifier can be used so that the total mass of the emulsifier is in the range of from 0.1 times to from 10 times the total mass of an oil component containing a carotenoid component in any form of the powder composition and the emulsified composition, preferably from 0.5 times to 8 times, particularly preferably from 0.8 times to 5 times, in view of the refinement of dispersed particles and the suppression of foaming. These ranges make it possible to provide good dispersion stability of the composition.

Among the emulsifiers, a nonionic surfactant is preferred because of, e.g., being low-irritative and having a low impact on the environment. Examples of the nonionic surfactant include sucrose fatty acid esters, polyglycerol fatty acid esters, organic acid monoglycerides, propylene glycol fatty acid esters, polyglycerol condensed ricinolate, sorbitan fatty acid esters, polyoxyethylene sorbitan fatty acid esters, and the like.

In a sucrose fatty acid ester, the sucrose fatty acid esters are those in which the carbon number of a fatty acid of the sucrose fatty acid ester is preferably from 12 to 20, and more preferably from 14 to 16, from the viewpoint of the stability of dispersed particles in the composition.

Preferred examples of the sucrose fatty acid ester include sucrose dioleate, sucrose distearate, sucrose dipalmitate, sucrose dimyristate, sucrose dilaurate, sucrose monooleate, sucrose monostearate, sucrose monopalmitate, sucrose monomyristate, sucrose monolaurate, and the like, and, among them, sucrose monooleate, sucrose monostearate, sucrose monopalmitate, sucrose monomyristate, and sucrose monolaurate are more preferred.

In accordance with the present invention, these sucrose fatty acid esters may be used alone or in combination.

The aqueous phase composition may contain a polyglycerol fatty acid ester as well as the specific polyglycerol fatty acid ester described above.

Such a polyglycerol fatty acid ester is an ester of polyglycerol having an average degree of polymerization of 2 or more, preferably from 6 to 15, and more preferably from 8 to 10, with a fatty acid having from 8 to 18 carbon atoms, such as caprylic acid, capric acid, lauric acid, myristic acid, palmitic acid, stearic acid, oleic acid, or linoleic acid.

Preferred examples of the polyglycerol fatty acid ester include hexaglyceryl monooleate, hexaglyceryl monostearate, hexaglyceryl monopalmitate, hexaglyceryl monomyristate, hexaglyceryl monolaurate, decaglyceryl monooleate, decaglyceryl monostearate, decaglyceryl monopalmitate, decaglyceryl monomyristate, decaglyceryl monolaurate, and the like.

Among them, more preferred are decaglyceryl monooleate (HLB=12), decaglyceryl monostearate (HLB=12), decaglyceryl monopalmitate (HLB=13), decaglyceryl monomyristate (HLB=14), decaglyceryl monolaurate (HLB=16), and the like.

These polyglycerol fatty acid esters may be used alone or in combination.

The sorbitan fatty acid ester according to the present invention is preferably a fatty acid ester whose fatty acid has 8 or more carbon atoms, more preferably 12 or more carbon atoms. Preferred examples of the sorbitan fatty acid ester include sorbitan monocaprylate, sorbitan monolaurate, sorbitan monostearate, sorbitan sesquistearate, sorbitan tristearate, sorbitan isostearate, sorbitan sesquiisostearate, sorbitan oleate, sorbitan sesquioleate, sorbitan trioleate, and the like.

In accordance with the present invention, these sorbitan fatty acid esters may be used alone or in combination.

The polyoxyethylene sorbitan fatty acid ester is preferably a fatty acid ester whose fatty acid has 8 or more carbon atoms, more preferably 12 or more carbon atoms. Further, the length (the number of added moles) of ethylene oxide in polyoxyethylene is preferably from 2 to 100, more preferably from 4 to 50.

Preferred examples of the polyoxyethylene sorbitan fatty acid ester include polyoxyethylene sorbitan monocaprylate, polyoxyethylene sorbitan monolaurate, polyoxyethylene sorbitan monostearate, polyoxyethylene sorbitan sesquistearate, polyoxyethylene sorbitan tristearate, polyoxyethylene sorbitan isostearate, polyoxyethylene sorbitan sesquiisostearate, polyoxyethylene sorbitan oleate, polyoxyethylene sorbitan sesquioleate, polyoxyethylene sorbitan trioleate, and the like.

These polyoxyethylene sorbitan fatty acid esters may be used alone or in combination.

Furthermore, a phospholipid such as lecithin may also be contained as an emulsifier in accordance with the present invention.

The phospholipid which can be used in the present invention contains a glycerine backbone as well as a fatty acid residue and a phosphate residue as essential components, to which a base, a polyhydric alcohol, and the like are bound, and is also referred to as lecithin. The phospholipid has a hydrophilic group and a hydrophobic group in the molecule and, therefore, has been conventionally widely used as an emulsifier in the fields of food products, pharmaceutical products, and cosmetics, A substance in which purity of lecithin is 60% or more is industrially utilized as lecithin and can also be used in the present invention; however, from the viewpoint of the formation of a fine oil droplet particle diameter and the stability of a functional oil component, a material that is generally called high-purity lecithin is preferable. This material has lecithin purity of 80% or more, and more preferably 90% or more.

Examples of phospholipids may include conventionally-known various phospholipids obtained by extraction and separation from the living bodies of plants, animals and microorganisms.

Specific examples of such phospholipids include, e.g., various lecithins derived from plants such as soybean, corn, peanut, rapeseed, wheat, and the like, animals such as egg yolk and cattle, microorganisms such as *Escherichia coli*, and the like.

Examples of lecithin identified by compound names include glycerolecithins such as phosphatidic acid, phosphatidylglycerin, phosphatidylinositol, phosphatidylethanolamine, phosphatidylmethylethanolamine, phosphatidylcholine, phosphatidylserine, bisphosphatidic acid, and diphosphatidylglycerin (cardiolipin); sphingolecithin such as sphingomyelin; and the like.

Further, in the present invention, in addition to the above-described high-purity lecithin, hydrogenated lecithin, enzyme-degraded lecithin, enzyme-degraded hydrogenated lecithin, hydroxylecithin, and the like may be used. These lecithins which may be used in the present invention may be used alone, or in the form of a mixture of plural kinds.

In a case in which the carotenoid-containing composition of the present invention is a powder composition, it is preferable to contain a water-soluble encapsulating agent in order to protect an oil droplet during a powderization process in drying or during the storage of a powder. As a result, an oil droplet particle diameter can be maintained in a fine state and the deterioration of the carotenoid component in an oil droplet can be reduced.

Further, when a powder composition is redissolved in water, the water-soluble encapsulating agent enables the water-dispersibility of an oil component to be made to be good and the transparency of the carotenoid-containing composition after the redissolution to be made to be good.

The water-soluble encapsulating agent is preferably at least one polysaccharide selected from fructose polymers and oligomers composed of sugar units containing at least two fructose units (hereinafter simply referred to as "fructose polymer or oligomer").

The fructose polymer or oligomer according to the present invention refers to a polymer or oligomer that contains fructose as a repeating unit and includes a sugar unit in which plural sugar units are bound by dehydrative condensation. In accordance with the present invention, the polysaccharide in which the number of the sugar repeating units containing fructose units is less than 20 is referred to as a fructose oligomer and the polysaccharide in which the number of sugar repeating units containing fructose units is 20 or more is referred to as a fructose polymer.

The number of the sugar repeating units is preferably from 2 to 60 and more preferably from 4 to 20, from the viewpoint of drying suitability and oil droplet miniaturization during resolubility. Water hydroscopic property is not too strong and adherence to a drying container in a drying process to reduce a recover rate can be effectively prevented when the number of repeating units (polymerization degree of fructose) is two or more, while an oil droplet particle diameter can be effectively prevented from coarsening during water redissolution when the number is 60 or less.

The fructose polymer or oligomer may also contain another monosaccharide as well as a fructose at the end or in a chain of the molecule. Examples of other monosaccharide units that can be contained include, but are not limited to, glucose (grape sugar), galactose, mannose, idose, altrose, gulose, talose, allose, xylose, arabinose, lyxose, ribose, threose, erythrose, erythrulose, xylulose, ribulose, psicose, sorbose, tagatose, and the like. Among these monosaccharides, glucose is preferred from the viewpoint of availability. Further, the presence of the monosaccharide at the end of the fructose chain as a bonding site is preferred from the viewpoint of the miniaturization of oil droplets during redissolution.

In the case of containing a saccharide other than fructose, the content ratio thereof is 50% or less, preferably 30% or less, by polymerization degree with respect to the number of fructose units, from the viewpoint of drying suitability and the miniaturization of oil droplets during resolubility.

Examples of water-soluble encapsulating agents preferably used in the present invention include inulin from the viewpoint of storage stability of a colorant, availability, and the like. Inulin in accordance with the present invention refers to fructose polymer or oligomer having one glucose at the end of the molecule. Inulin is known to be present widely in the natural world and is contained abundantly in *Cichorium endivia*, Jerusalem artichoke, dahlia, garlic, leek, onion, and the like. The details of inulin are described in Handbook of Hydrocolloids, G. O. Phillips, P. A. Williams Ed., 397-403, (2000) CRC Press. Generally, the chain length is represented by expression the glucose unit as G and the fructose unit as F. Inulin in accordance with the present invention does not contain any sucrose represented as GF.

Inulins extracted from natural sources are typically polymers or oligomers from GF2 (kestose), GF3 (nystose), GF4 (fructosylnystose) to around GF60, or mixtures thereof.

In accordance with the present invention, examples of inulins include commercially available products powdered by the condensation and spray-drying of aqueous solutions of inulins separated and hot-water extracted from the roots of *Cichorium endivia*, Jerusalem artichoke, dahlia, and the like. Examples thereof may include FRUTAFIT (manufactured by SENSUS) extracted from a root of *Cichorium endivia*, BENEO (ORAFTI) extracted from a root of *Cichorium endivia*, a reagent derived from a dahlia root (Wako Pure Chemical Industries, Ltd., and Sigma Ltd.), a reagent extracted from a root of *Cichorium endivia* (Sigma Ltd.), and the like.

Further, the fructose oligomer or polymer in accordance with the present invention may also include a product that is prepared from sucrose using dislocation activity of fructan in β-fructofuranosidase. Examples thereof may include FUJI FF (manufactured by Fuji Nihon Seito Corporation) and GF2 (Meiji Seika).

Inulin used in the present invention is preferably from 2 to 60 in terms of the number of repeating units of fructose (polymerization degree) from the viewpoint of the miniaturization of oil droplets during redissolution, and the polymerization degree of fructose is more preferably from 4 to 20 from the viewpoint of adhesiveness to an apparatus during spray-drying and solubility in water.

It is preferable that the fructose polymer or oligomer of the present invention already be added at the time of emulsification, however a partial or all of the fructose polymer or oligomer may also be added after emulsification.

Also, another water-soluble polymer or oligomer may be used in combination with the fructose polymer or oligomer. Examples of other water-soluble polymers and oligomers include, but are not limited to, agarose, starch, carrageenan, gelatin, xanthan gum, gellan gum, galactomannan, casein, tragacanth gum, xyloglucan, β-glucan, curdlan, water-soluble soybean fiber, chitosan, alginic acid, sodium alginate, and the like.

The content of the water-soluble encapsulating agent in the carotenoid-containing composition is, by mass ratio, preferably from 0.5 times to 50 times the total mass of oil components in the composition, more preferably from 1 time to 20 times, further preferably from 1 time to 10 times, more further preferably from 2 times to 5 times, from the viewpoints of retention of shape and solubility.

In addition, the water-soluble encapsulating agent may be contained in the aqueous phase of the carotenoid-containing composition, may also be contained as the aqueous phase composition during pressurization emulsification described below, or may be added to the aqueous phase of the carotenoid-containing composition after pressurization emulsification.

[Other Addition Components]

Besides the above-described components, components that are commonly used in the fields of food products, cosmetics, and the like may also be appropriately blended in the carotenoid-containing composition of the present invention depending on the form of the composition. The addition components may be blended as components of the oil phase component mixed liquid, the carotenoid-containing oil phase composition, or the aqueous phase composition depending on the properties of the addition components, or may be blended as addition components to the aqueous phase of the carotenoid-containing composition.

Examples of such other components may include polyhydric alcohols such as glycerol and 1,3-butylene glycol; monosaccharides or polysaccharides such as glucose, fructose, lactose, maltose, sucrose, pectin, κ-carrageenan, locust bean gum, guar gum, hydroxypropyl guar gum, xanthan gum, karaya gum, tamarind seed polysaccharide, gum arabic, tragacanth gum, hyaluronic acid, sodium hyaluronate, sodium chondroitin sulfate, and dextrin; sugar alcohols such as sorbitol, mannitol, maltitol, lactose, maltotriitol, and xylitol; inorganic salts such as sodium chloride and sodium sulfate; proteins having molecular weight of more than 5000 such as casein, albumin, methylated collagen, hydrolyzed collagen, water-soluble collagen, and gelatin; synthetic polymers such as carboxyvinyl polymers, sodium polyacrylate, polyvinyl alcohol, polyethylene glycol, and ethylene oxide-propylene oxide block copolymer; water-soluble cellulose derivatives such as hydroxyethyl cellulose methyl cellulose; flavonoids (catechin, anthocyanin, flavone, isoflavone, fravane, flavanone, rutin), lignanes, curcumins, coumarins, and the like, and the other components may also be contained, based on the functions thereof, for example, as functional components, excipients, viscosity modifiers, radical scavengers, and the like.

In addition, for example, other additives that are typically used for the intended use, such as various medicinal effective components, pH adjusters, pH buffers, ultraviolet ray absorbers, antiseptic agents, perfumes, coloring agents, may be used in combination.

[Method for Producing Carotenoid-Containing Composition]

The carotenoid-containing composition of the present invention can be obtained by a production method including: obtaining an oil phase component mixed liquid by mixing the carotenoid component containing the crystalline carotenoid, the (poly)glycerol fatty acid ester and the phenolic antioxidant (referred to as oil phase component mixing process); and heating the oil phase component mixed liquid under a condition of a temperature of not less than the dissolution temperature (melting point) of the carotenoid component (referred to as oil phase component heating process).

According to this production method, the phenolic antioxidant is present in a reaction system during heating at a temperature of not less than the dissolution temperature (melting point) of the non-crystalline carotenoid component and, therefore, the decomposition or disappearance of the crystalline carotenoid in the carotenoid component during the heating process may be suppressed. Further, since the carotenoid component is heated together with the phenolic antioxidant and the (poly)glycerol fatty acid ester, the non-crystalline state of the crystalline carotenoid in the carotenoid component may be stably maintained.

In the oil phase component mixing process, each oil phase component that constitutes the carotenoid-containing composition as an oil phase composition is mixed. The mixing of the oil phase component is not particularly limited. The oil phase component mixed liquid is obtained by the oil phase component mixing process.

In the oil phase component heating process, the oil phase component mixed liquid is heated under a condition of a temperature of not less than the dissolution temperature (melting point) of the carotenoid component. It is necessary that the temperature at which the oil phase component mixed liquid is heated is a temperature that is not less than the dissolution temperature (melting point) of the carotenoid component. When the temperature is less than the dissolution temperature (melting point) of the carotenoid component, a crystalline carotenoid does not dissolve, so that a large amount of a crystal substance becomes present in the carotenoid-containing composition. In the oil phase component heating process, the crystalline carotenoid is co-dissolved together with the (poly)glycerol fatty acid ester and, therefore, a crystal substance may be dissolved at lower temperature.

The melting point of the carotenoid component means a temperature at which a crystalline carotenoid in the carotenoid component dissolves. In a case in which the carotenoid component is constituted by a crystalline carotenoid alone, a melting point of the crystalline carotenoid corresponds to the melting point of the carotenoid component. Meanwhile, in a case in which components other than a crystalline carotenoid are contained in the carotenoid component, a melting point of the carotenoid component means a temperature at which a carotenoid in the carotenoid component dissolves.

For example, it is known that in a case in which carotenoid-containing oil derived from a natural product is used as a carotenoid component, impurities and the like may be contained, so that a crystalline carotenoid in the carotenoid component dissolves at a temperature lower than the melting point of the crystalline carotenoid. In this case, the temperature at which the crystalline carotenoid in the carotenoid component dissolves corresponds to the "melting point of the carotenoid component" in accordance with the present invention.

The melting point of the carotenoid component may be confirmed by a method generally used for confirming a melting point and may be confirmed, for example, by DSC.

The heating temperature (co-dissolution temperature) to be applied to the oil phase component heating process varies depending, specifically, on the kind of a crystalline carotenoid, a carotenoid component, or the like to be used. Generally, however, in a the case of the carotenoid component containing lycopene, the heat temperature may be from 150° C. to 200° C., and from the viewpoint of suppressing thermal decomposition, preferably from 150° C. to 180° C., more preferably from 150° C. to 170° C.

Further, as for the maximum heating temperature to be applied to the oil phase component heating process, from the viewpoint of suppressing decomposition of a crystalline carotenoid, the highest temperature in heat treatment is a temperature such that a difference from a dissolution temperature (melting point) of the carotenoid component is preferably 15° C. or less and a difference from a dissolution temperature (melting point) of the carotenoid component is more preferably 12° C. or less.

The heating time to be applied to the oil phase component heating process may be time for which a carotenoid component is dissolved in the oil phase component mixed liquid and is preferably from 10 minutes to 60 minutes and more preferably from 15 minutes to 45 minutes from the viewpoint of efficiently suppressing the amorphization of a crystal substance and the decomposition of a crystalline carotenoid due to excessive heat, but the heating time is not limited thereto.

In addition, it is important to carry out the oil phase component heating process so that the oil phase component mixed liquid in its entirety has uniform temperature, therefore, sufficient stirring while heating is preferred, and it is desirable to maintain at a definite temperature by using an airtight container and heating while stirring.

By the oil phase component heating process, the carotenoid-containing composition as an oil phase composition is obtained.

From the viewpoint of more surely suppressing the decomposition or disappearance of a crystalline carotenoid in a production process, the method for producing the carotenoid-containing composition is preferably any of the following embodiments:

(1) a production method including: obtaining an oil phase component mixed liquid by mixing the carotenoid component containing the crystalline carotenoid, the (poly)glycerol fatty acid ester and the phenolic antioxidant; and heating the oil phase component mixed liquid under a condition of a temperature of not less than a dissolution temperature (melting point) of the carotenoid component and the maximum temperature such that a difference from the dissolution temperature (melting point) of the carotenoid component is 10° C. or less for from 15 minutes to 45 minutes;

(2) a production method including: obtaining an oil phase component mixed liquid by mixing the carotenoid component including lycopene, the (poly)glycerol fatty acid ester and the phenolic antioxidant; and heating the oil phase component mixed liquid under a condition of a temperature of from 150° C. to 170° C.; and (3) a production method including: obtaining an oil phase component mixed liquid by mixing the carotenoid component including lycopene, the (poly)glycerol fatty acid ester, the phenolic antioxidant which is a cinnamic acid and an ascorbic acid-based antioxidant which is at least one selected from ascorbic acid and ascorbic acid esters; and heating the oil phase component mixed liquid under a condition of a temperature of from 150° C. to 170° C.

In the preferred embodiments described above, the carotenoid component, the (poly)glycerol fatty acid ester and the phenolic antioxidant that constitute the oil phase component mixed liquid, and the ascorbic acid-based antioxidant are further preferably the same as the carotenoid component, the (poly)glycerol fatty acid ester, the phenolic antioxidant, and the ascorbic acid-based antioxidant in the preferred embodiments in the carotenoid-containing composition.

[Method for Producing Emulsified Composition]

In a case in which the carotenoid-containing composition of the present invention is an emulsified composition, the method may include an emulsification process of mixing the oil phase composition obtained in the oil phase component heating process with an aqueous phase composition including an aqueous phase component and performing emulsification after the oil phase component heating process. By this method, an oil-droplet-in-water type emulsified composition in which an oil phase component containing a carotenoid component is finely dispersed as oil droplets (emulsified particles) in water can be obtained. In the emulsified composition, the carotenoid component containing a crystalline carotenoid is maintained stably.

Although the ratio (mass) of an oil phase and an aqueous phase in the emulsification is not particularly limited, the ratio (% by mass) of oil phase/aqueous phase is preferably from 0.1/99.9 to 50/50, more preferably from 0.5/99.5 to 30/70, further preferably from 1/99 to 20/80.

By setting the ratio of oil phase/aqueous phase to 0.1/99.9 or more, reduction in active components is prevented, which results in a favorable trend that a practical problem of the emulsion composition is not caused. Further, by setting the ratio of oil phase/aqueous phase to 50/50 or less, reduction in concentration of the emulsifier is prevented, which results in a favorable trend that emulsion stability of the emulsified composition is not deteriorated.

The emulsification may be performed by one step-operation of the emulsification; however, it is preferable to perform two or more step-operations of the emulsification, from the viewpoint of obtaining uniform and fine emulsified particles.

Specifically, it is particularly preferable to use a combination of two or more kinds of emulsification devices in a manner such that emulsification is performed by way of a high-pressure homogenizer or the like in addition to the one step-operation of the emulsification in which emulsification is performed using an ordinary emulsification apparatus (for example, stirrer, impeller stirring, homomixer, continuous-flow type shearing apparatus) utilizing a shearing action. By using a high-pressure homogenizer, the emulsion can be aligned with further uniform and fine particles of droplets. Further, plural operations may be additionally performed in order to make the particle diameter of oil droplets more uniform.

As emulsification means that can be used herein, use can be made of any of generally known emulsification techniques such as spontaneous emulsion methods, interfacial chemical emulsion methods, electric emulsion methods, capillary emulsion methods, mechanical emulsion methods, and ultrasonic emulsion methods and the like.

As a useful method for making the emulsion particles finer, an interfacial chemical emulsion method such as a PIT emulsion method, a gel emulsion method and the like is known. This method has an advantage in that consumption energy is low, and therefore the method is suitable in the case of finely emulsifying a material that is easy to deteriorate by heat.

Further, as a generally-used emulsion method, a method of using a mechanical force is applied, that is, the method of tearing apart oil droplets by applying a shearing force thereto from the outside. The most-general force of the mechanical force is a high-speed and high-shearing stirring machine. As such a stirring machine, stirring machines that are called homomixers, disper mixers, and ultramixers are commercially available.

As another mechanical emulsification apparatus that is useful for particle-diameter reduction, a high-pressure homogenizer is available and various kinds of apparatuses are commercially available. The high-pressure homogenizer is capable of applying greater shearing force than a stirring method, and, therefore, even if the amount of an emulsifier is relatively small, particle-diameter reduction may be realized.

There are main types of high-pressure homogenizer: one is a chamber type high-pressure homogenizer having a fixed throttling section and a homogeneous valve type high-pressure homogenizer in which the divergence of throttle is controlled.

Examples of the chamber type high-pressure homogenizer include MICROFLUIDIZER (manufactured by Microfluidics Corporation), NANOMIZER (manufactured by Yoshida Kikai Co., Ltd.), ALTIMIZER (manufactured by Sugino Machine Limited), and the like.

Examples of the homogeneous valve type high-pressure homogenizer include Gaulin-type homogenizer (manufactured by APV), Rannie-type homogenizer (manufactured by Rannie), HIGH-PRESSURE HOMOGENIZER (manufactured by Niro Soavi), HOMOGENIZER (manufactured by SANWA MACHINERY TRADING CO., LTD.), HIGH-PRESSURE HOMOGENIZER (manufactured by IZUMI FOOD MACHINERY CO., LTD.), ULTRAHIGH-PRESSURE HOMOGENIZER (manufactured by IKA Corporation), and the like.

There is an ultrasonic homogenizer as a dispersing apparatus having a relatively good energy efficiency and an emulsification apparatus having a simple structure. Examples of a high-power ultrasonic homogenizer that can be produced include ultrasonic homogenizer US-600, ibid. US-1200T, ibid. RUS-1200T and ibid. MUS-1200T (all manufactured by NIHONSEIKI KAISHA LTD.), ultrasonic processor UIP 2000, ibid. UIP 4000, ibid. UIP 8000 and ibid. UIP 1600 (all manufactured by Heilscher), and the like. These high-power ultrasonic homogenizers are used at frequency of 25 kHz or less, and preferably at frequency of from 15 to 20 kHz.

Further, as other known emulsifying means, a method of using an apparatus that does not include an extraneous stirring section and needs only low energy is also useful and examples of the apparatus include static mixers, micro channels, micro mixers, membrane emulsification apparatuses, and the like.

The temperature condition at the time of emulsion dispersion in the present invention is not particularly limited but, from the viewpoint of the stability of functional oil components, is preferably from 10 to 100° C., and a preferable range can be appropriately selected depending on a dissolution temperature (melting point) of the functional oil component to be handled.

Further, in the case of using a high-pressure homogenizer in the present invention, the pressure is preferably 50 MPa or more, more preferably from 50 MPa to 280 MPa, further preferably from 100 MPa to 280 MPa, and the processing is preferably performed at this pressure.

Further, from the viewpoint of keeping particle diameter of the dispersion particles, it is preferred that an emulsified liquid that is an emulsion dispersed composition is cooled through some sort of cooling machine within 30 seconds, preferably within 3 seconds immediately after the emulsified liquid has passed through a chamber.

The production method may include drying the oil-in-water emulsified dispersion obtained in an emulsification process to obtain a powder composition (hereinafter may be referred to as "powderization process"). This method makes it possible to obtain a carotenoid-containing composition as a powder composition. The carotenoid-containing composition as a powder composition is a composition that has storage stability due to the powderization form, and in addition, a composition in which crystallization of crystalline carotenoid has been suppressed in the powder composition as well as the emulsified composition in which the powder composition has been re-dissolved in an aqueous medium.

As for the drying means used in the powderization process, known drying means may be used, and examples of the drying means include natural drying, heat drying, hot air drying, high-frequency drying, ultrasonic drying, reduced-pressure drying, vacuum drying, freeze drying, spray drying, and the like. These means may be used alone or in combination of two or more means.

In the present invention, reduced-pressure drying, vacuum drying, freeze drying, and spray drying are preferred since functional materials that are weak against heat are often contained. Further, as one of the vacuum drying methods, a method of conducting vacuum (reduced-pressure) drying while keeping a temperature of 0° C. or less and freezing temperature or higher is also preferred.

In the case of vacuum drying or reduced-pressure drying, the drying is preferably conducted by repeating concentration while gradually increasing the degree of reduced pressure in order to avoid scatter of the liquid due to bumping.

In the present invention, the freeze drying in which ice is sublimated from a material in a frozen state to remove water is preferred. The freeze drying method has a great advantage such that since the dry process usually proceeds at 0° C. or less, ordinarily at around −20° C. to −50° C., heat denaturation of the material is not caused, and in the course of water recovery, taste, color, nutritional value, shape, texture, and the like are easy to restore to their states before the drying.

Examples of the commercially available freeze dryer include, but are not limited to, FREEZE DRYER VD-800F (TAITEC Corporation), FLEXI-DRY MP (FTS SYSTEMS INC.), DURATOP/DURASTOP (FTS SYSTEMS INC.), TAKARA VACUUM FREEZE DRYER Model A (TAKARA ATM), DESKTOP FREEZE-DRYER FD-1000 (TOKYO RIKAKIKAI CO., LTD.), VACCUM FREEZE-DRYER FD-550 (TOKYO RIKAKIKAI CO., LTD.), VACCUM FREEZE-DRYER (Takara Seisakusho), and the like.

Further, in the present invention, a spray-drying method is particularly preferred as drying means from the viewpoint of a balance between production efficiency and quality. The spray drying is a sort of convective-hot air drying. The liquid composition is sprayed as fine particles of several 100 μm or less in a hot air and resultantly drops in a tower while being dried, whereby the composition is collected as a solid powder thereof. Though the material is temporarily exposed to hot air, increase of temperature does not become too high because of very short exposure time and vapor latent heat, and therefore heat denaturation of the material is not easy to be caused and a change due to water recovery is small as is the case with freeze drying. In the case of a material that is very weak against heat, it is also possible to feed cold air instead of hot air. In this case, relatively milder drying can be preferably realized, though the drying performance is reduced.

Examples of the commercially available spray dryer include, but are not limited to, a spray dryer SPRAY DRYER SD-1000 (TOKYO RIKAKIKAI CO., LTD.), SPRAY DRYER-8i (OHKAWARA KAKOHKI CO., LTD.), CLOSED SPRAY DRYER CL-12 (OHKAWARA KAKOHKI Co., LTD.), SPRAY DRYER ADL 310 (Yamato Scientific Co., Ltd.), MINISPRAY DRYER B-290 (BÜCHI), PJ-MiniMax (Powdering Japan), PHARMASD (GEA Niro), and the like.

Further, for example, like a fluid-bed granulation dryer MP-01 (POWREX CORPORATION) and a spray dryer with a built-in fluid-bed FSD (GEA Niro). It is also preferred to produce granular particles exerting excellent handling ability at the same time as drying with an apparatus by which both drying and granulation are performed at the same time.

The average particle diameter in the oil-in-water emulsified composition or a powder composition prepared by powdering the oil-in-water emulsified composition means a particle diameter of the dispersion particles (oil droplets) in the emulsified composition in the case of the oil-in-water emulsified composition, and means a particle diameter of the dispersion particles (oil droplets) in a 1% by mass aqueous solution (at the time of redissolution) in the case of the powder composition.

The particle diameter of the dispersion particles can be measured using a commercially-available particle diameter distribution measuring apparatus or the like. As for the particle diameter distribution measuring method for an emulsion, optical microscopy, laser confocal microscopy, electron microscopy, atomic force microscopy, static light-scattering method, laser diffractometry, dynamic light-scattering method, centrifugal sedimentation method, electric pulse measuring method, chromatography, ultrasonic attenuation method, and the like are known, and apparatuses in accordance with their principles are commercially available.

The dynamic light-scattering method is preferable in the particle diameter measurement of the dispersion particles from the viewpoints of particle diameter range and easiness of measurement in the present invention. Examples of the commercially-available measuring apparatus using the dynamic light-scattering method include NANOTRAC UPA (Nikkiso Co., Ltd.), dynamic light-scattering method particle diameter distribution measuring apparatus LB-550 (Horiba, Ltd.), concentrated system particle diameter analyzer FPAR-1000 (Otsuka Electronics Co., Ltd.), and the like, however, as the particle diameter in the present invention, a value obtained by measurement at 25° C. using the particle diameter analyzer FPAR-1000 (Otsuka Electronics Co., Ltd.) is adapted.

That is, in the measuring method of the particle diameter, the particle diameter in terms of median diameter (d=50) is measured using the particle diameter analyzer FPAR-1000 (Otsuka Electronics Co., Ltd.) in a manner such that in the case of the oil-in-water type composition, it is diluted 20-fold with pure water, meanwhile in a powder composition, it is diluted with pure water so that the solid content becomes 1% by mass.

Further, the particle diameter of the dispersion particles may be adjusted by factors such as stirring conditions in the production method (shearing force, temperature, pressure) and ratio of oil phase and aqueous phase, besides the components of the composition.

The particle diameter of the oil-in-water emulsified composition is preferably from 50 nm to 300 nm from the viewpoints of transparency and absorbability, and more preferably from 50 nm to 200 nm and most preferably from 50 nm to 150 nm from the viewpoint of transparency.

The carotenoid-containing composition of the present invention stably contains a crystalline carotenoid as a carotenoid component and is a carotenoid-containing composition such that a desirable effect due to the carotenoid may be fully expected. Accordingly, the carotenoid-containing composition may be preferably applied to a food composition, a cosmetic composition, and a pharmaceutical composition.

Foods, cosmetics, or the like containing the carotenoid-containing composition of the present invention has good storage stability of a carotenoid component and may exhibit an effect that may not be exerted due to the presence of a crystal substance, for example, good absorbability of carotenoid. Further, for example, in a case in which the carotenoid-containing composition of the present invention is used in a powder composition food product, the food can be preserved as a powdered food product for a long term.

As needed, a component that can be added to food products or cosmetics may be appropriately added to a food product or cosmetic containing the carotenoid-containing composition of the present invention.

The cosmetic composition is preferably used in, for example, lotion, beauty essence, milky lotion, cream pack mask, pack, shampoo cosmetics, fragrance cosmetics, liquid body cleaning preparations, UV care cosmetics, deodorant cosmetics, oral care cosmetics, and the like.

Further, as the foods, there can be preferably used not only common foods such as a nutrition-supplement drink, a revitalizer, a palatable drink, a frozen dessert, and the like, but also tablet-shaped, granule-shaped and capsule-shaped nutritional supplementary foods, and the like.

In the case of use for functional foods, although an addition amount of the powder composition according to the present invention cannot be simply generalized because it varies depending on the kind and the intended use of a product, the powder composition can be used by adding it so as to become in a range of from 0.01 to 10% by mass and preferably from 0.05 to 5% by mass, with respect to the product. If the addition amount is 0.01% by mass or more, exertion of a desired effect may be prospective and meanwhile if it is 10% by mass or less, appropriate effects may be often exerted efficiently.

EXAMPLES

The present invention will be described below with reference to examples but the present invention is not limited thereto. Note that the numerical numbers expressed by "part" and "%" in the following description are based on mass standard, unless otherwise specified.

Example 1

<Preparation of Oil Phase Composition>

Among the oil phase components described below, (5) and (3) were mixed and stirred at room temperature, and (2), (1), and (4) were further mixed and stirred while being added in this order, and were dissolved. Then, the temperature was increased for 30 minutes so that the temperature became from room temperature into the range of 155° C. to 165° C. while stirring, and the temperature was maintained at a temperature of 155° C. to 165° C. for 5 minutes, followed by cooled to room temperature to obtain a carotenoid-containing composition (oil phase composition 1). In addition, the dissolution temperature (melting point) of lycopene 18 is 153° C. (endothermic peak value in DSC measurement).

| Oil phase composition 1 | |
|---|---|
| (1) Lycopene paste (lycopene concentration: 18%) *[1] | 1.00 part |
| (2) Diglyceryl monostearate *[2] | 0.20 part |
| (3) Ferulic acid *[3] | 0.30 part |
| (4) Calcium ascorbate 50% solution *[4] | 0.80 part |
| (5) Tri (caprylic acid/capric acid) glyceryl *[5] | 0.50 part |

*[1] Kyowa Wellness Co., Ltd., "LYCOPENE 18" (molecular weight of 537.0)
*[2] Nikko Chemicals Co., Ltd., "NIKKOL DGMS" (HLB = 5.0)
*[3] Tsuno Food Industrial Co., Ltd. (molecular weight of 194)
*[4] Molecular weight of 390 (as anhydride)
*[5] Kao Corporation "COCONARD MT" (HLB = 1)

Examples 2 to 7 and Comparative Examples 1 to 7

In Examples 2 to 7, Comparative Examples 1 to 2, and Comparative Examples 4 to 6, oil phase compositions 2 to 9 and 11 to 13 were obtained in the same manner as in Example 1 except that the kinds and contents of the oil phase components were changed as listed in Table 1.

In Comparative Example 3, an oil phase composition 10 was obtained in the same manner as in Example 1 except that each oil phase component listed in Table 1 was stirred and mixed while being warmed from room temperature to 90° C. to 110° C. and was maintained at 90° C. to 110° C. for 5 minutes.

In Comparative Example 7, an oil phase composition 14 was obtained by warming from room temperature to 155° C. to 165° C. for 25 minutes and maintenance for 5 minutes in the same manner as in Example 1 except that only the lycopene 18 paste used in Example 1 was used.

As each component in Table 1, there were used the following components:

Glyceryl monostearate: NIKKOL MGS-F40V Nikko Chemicals Co., Ltd.
Tetraglyceryl tristearate: NIKKOL Tetraglyn 3-S Nikko Chemicals Co., Ltd.
Tetraglyceryl pentastearate: NIKKOL Tetraglyn 5-S Nikko Chemicals Co., Ltd.
Hexaglyceryl tristearate: NIKKOL Hexaglyn 3-S Nikko Chemicals Co., Ltd.
Hexaglyceryl pentastearate: NIKKOL Hexaglyn 5-SV Nikko Chemicals Co., Ltd.
Decaglyceryl monooleate: NIKKOL Decaglynl-OV Nikko Chemicals Co., Ltd.

γ-Orizanol: Tsuno Food Industrial Co., Ltd. Co., Ltd. (molecular weight of 602.89)
Gallic acid: molecular weight of 170.12
α-Glucosyl rutin: molecular weight of 10000 (610-1218)
Disodium ethylenediaminetetraacetate: molecular weight of 372.24 (dihydrate)

A numerical value indicating the blending amount of each component in Table 1 represents "parts(s)".

(2) Evaluation of Crystal by Observation by Polarizing microscope

Visual observation of each oil phase composition just after the preparation thereof was conducted using PCLIPSE LV100POL (Nikon Corporation). The evaluation results of the visual observation were classified as follows.

Visual Evaluation A: Almost no crystal derived from lycopene is found.

TABLE 1

|   |   | Example 1 | Example 2 | Example 3 | Example 4 | Example 5 | Example 6 | Example 7 |
|---|---|---|---|---|---|---|---|---|
| (1) | Lycopene paste (Lycopene content: 18%) | 1.00 | 1.00 | 1.00 | 1.00 | 1.00 | 1.00 | 1.00 |
| (2) | Glyceryl monostearate |  | 0.20 |  |  |  |  |  |
|   | Diglyceryl monostearate | 0.20 |  |  |  |  |  | 0.10 |
|   | Tetraglyceryl tristearate |  |  |  |  | 1.80 |  |  |
|   | Tetraglyceryl pentastearate |  |  |  | 0.002 |  |  |  |
|   | Hexaglyceryl tristearate |  |  |  |  |  | 0.10 |  |
|   | Hexaglyceryl pentastearate |  |  | 0.20 |  |  |  |  |
|   | Decaglyceryl monooleate |  |  |  |  |  |  |  |
| (3) | Ferulic acid | 0.30 | 0.09 |  |  | 0.30 | 0.15 | 0.40 |
|   | γ-Orizanol |  |  | 0.90 |  |  |  |  |
|   | Gallic acid |  |  |  | 0.30 |  |  |  |
|   | α-Glucosyl rutin |  |  |  |  |  |  |  |
| (4) | Ascorbic acid Ca (50%) | 0.80 | 1.80 | 0.18 | 0.80 | 1.00 | 1.00 |  |
|   | Disodium ethylenediaminetetraacetate |  |  |  |  |  |  |  |
| (5) | Tri(caprylic acid/capric acid)glyceryl | 0.50 |  | 0.50 | 0.50 | 0.50 | 1.00 | 1.50 |
|   | Olive oil |  | 0.50 |  |  |  |  |  |
| Warming treatment |  |  |  |  |  |  |  |  |
| Set temperature |  | 155-165° C. | 155-165° C. | 155-165° C. | 155-65° C. | 155-165° C. | 155-165° C. | 155-165° C. |
| Heating-up time (min) |  | 30 | 30 | 30 | 30 | 30 | 30 | 30 |
| Retention time (min) |  | 5 | 5 | 5 | 5 | 5 | 5 | 5 |
| (3)/(1) [mole time(s)] |  | 4.61 | 1.38 | 4.45 | 13.80 | 4.61 | 2.31 | 6.15 |
| (4)/(1) [mole time(s)] |  | 3.06 | 6.88 | 0.69 | 3.06 | 3.82 | 3.82 | 0.00 |

|   |   | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|
| (1) | Lycopene paste (Lycopene content: 18%) | 1.00 | 1.00 | 1.00 | 1.00 | 1.00 | 1.00 | 1.00 |
| (2) | Glyceryl monostearate |  |  |  |  |  | 0.15 | 0.10 |
|   | Diglyceryl monostearate |  | 0.20 |  |  |  |  |  |
|   | Tetraglyceryl tristearate |  |  |  |  |  |  |  |
|   | Tetraglyceryl pentastearate |  |  | 0.20 |  |  |  |  |
|   | Hexaglyceryl tristearate |  |  |  |  |  |  |  |
|   | Hexaglyceryl pentastearate |  |  |  |  |  |  |  |
|   | Decaglyceryl monooleate |  |  |  | 1.00 |  |  |  |
| (3) | Ferulic acid |  |  |  |  |  |  |  |
|   | γ-Orizanol |  |  |  |  |  |  |  |
|   | Gallic acid |  |  |  |  |  |  |  |
|   | α-Glucosyl rutin |  |  |  |  |  | 1.50 |  |
| (4) | Ascorbic acid Ca (50%) | 0.80 |  | 1.80 | 1.00 | 1.60 |  |  |
|   | Disodium ethylenediaminetetraacetate |  |  |  |  |  |  | 2.00 |
| (5) | Tri(caprylic acid/capric acid)glyceryl | 0.50 | 0.50 |  |  |  |  |  |
|   | Olive oil |  |  |  | 1.00 |  |  |  |
| Warming treatment |  |  |  |  |  |  |  |  |
| Set temperature |  | 155-165° C. | 155-165° C. | 155-165° C. | 155-165° C. | 155-165° C. | 155-165° C. | 155-165° C. |
| Heating-up time (min) |  | 30 | 30 | 30 | 30 | 30 | 30 | 30 |
| Retention time (min) |  | 5 | 5 | 5 | 5 | 5 | 5 | 5 |
| (3)/(1) [mole time(s)] |  | 0.00 | 0.00 | 0.00 | 0.00 | 0.00 | 0.00 | — |
| (4)/(1) [mole time(s)] |  | 3.06 | 0.00 | 6.88 | 3.82 | 6.11 | 17.75 | — |

<Evaluation>

Evaluation of the oil phase compositions 1 to 14 obtained as described above were conducted as follows. These evaluation results are listed in Table 2.

(1) DSC Endothermic Peak Temperature

DSC Q2000 (TA Instruments Japan Inc.) was used. Endothermic and exothermic temperatures for each oil phase composition were determined in one cycle of temperature-rise to temperature-fall (15° C./min) in the temperature range of 30° C. to 200° C.

B: Crystals derived from lycopene are scattered, but to a minor extent.

C: Crystals derived from lycopene are present throughout the observed image.

(3) Lycopene Residual Rate

Each oil phase composition was diluted 1062-fold with acetone in order to effect a lycopene concentration of 0.005% by volume and was dissolved sufficiently. Then, after filtration through a filter of 0.45 μm, the absorbance of the filtrate at the maximum peak wavelength (465 nm to 475 nm) was measured with a spectrophotometer V-630 (manufactured by JASCO Corporation).

Evaluation was conducted by diluting LYCOPENE 18 with acetone to have a lycopene concentration of 0.005% by volume and measuring the absorbance at the peak wavelength in the same manner as above, and the percentage when the intensity of this lycopene was taken as 100% was defined as the lycopene residual rate of each oil phase composition.

Further, a lycopene residual ratio was measured in the same manner as described above after storage of each oil phase composition at 40° C. for 4 months.

(4) Dynamic Absorbability

The oil phase compositions 1 to 14 were diluted to have a lycopene concentration of 2 mg/ml, the resultant was orally administered (each group: n=4) to a non-fasted 6 week-old male rat at a dose of 10 ml/kg, and then, after each of 1, 2, 3, 4, 6, 8, and 24 h, 0.4 ml of blood was collected. The oil phase composition 14 was prepared with tri(caprylic acid/capric acid)glyceryl (COCONAD MT) to have a lycopene concentration of 2 mg/mL, followed by administering the resultant to a rat to collect blood after the administration in the same manner as in the case of the oil phase compositions 1 to 13.

The collected blood was centrifuged and 0.1 ml of plasma was taken from the supernatant. The plasma was dissolved in acetone, and then hexane was added, the mixture was left to stand, and the supernatant liquid was recovered. The recovered supernatant was dried by solidification, and then the solid was redissolved in chloroform/methanol=1/1 (v/v), and the content of lycopene was measured by HPLC.

The relationship between the time from administration to collection of blood and the plasma lycopene concentration was illustrated graphically, and an AUC (area under the blood concentration-time curve) over a period of 8 hours from administration with respect to each administered composition was determined as a dynamic absorption value. The results are listed in Table 2 below. A higher numerical number is evaluated as a higher concentration of active components in the blood.

DSC endothermic peak was found and crystallization was suppressed, and contained the phenolic antioxidant, and therefore indicated high lycopene residual rates not only just after the preparation but also after 4-month storage at 40° C.

Further, the results of administration experiments on rats demonstrated that all of the oil phase compositions of Example 1 to Example 7 exhibited excellent lycopene absorbability and were carotenoid-containing compositions exhibiting high absorbability due to the suppression of lycopene crystallization.

In contrast, in all of Comparative Example 1 excluding the specified (poly)glycerol fatty acid ester and Comparative Examples 2 to 7 excluding the phenolic antioxidant, lycopene was not able to be stably maintained. Further, in Comparative Example 8, lycopene was not able to be stably maintained in $\alpha$-glucosyl rutin in which a lot of phenolic hydroxyl groups were present in the antioxidant unlike the specific phenolic antioxidant having one phenolic hydroxyl group in the molecule.

Further, oil-in-water emulsified compositions that may contain carotenoid components as an oil-in-water emulsified particles can be provided by emulsification-mixing the oil phase compositions of Example 1 to Example 7, for example, with an aqueous phase composition containing a cane sugar laurate ester with HLB=16. This oil-in-water emulsified composition can also stably contain lycopene as a carotenoid component in an non-crystalline state in the same manner as in the case of the oil phase compositions of Example 1 to Example 7.

Thus, according to the present invention, a carotenoid-containing composition that stably contains a high-crystalline carotenoid as a non-crystalline carotenoid component can be provided.

The disclosure of Japanese Patent Application No. 2011-033812, filed on Feb. 18, 2011, is incorporated herein by reference in its entirety.

All literatures, patent applications, and technical standards described herein are herein incorporated by reference to the same extent as if each individual literature, patent

TABLE 2

|  | Example 1 | Example 2 | Example 3 | Example 4 | Example 5 | Example 6 | Example 7 | Comparative Example 1 |
|---|---|---|---|---|---|---|---|---|
| DSC absorption peak temperature | none | none | none | none | none | none | none | 153° C. |
| Observation by polarizing microscope | A | A | A | B | A | A | A | C |
| Lycopene residual rate (just after preparation) | 99% | 100% | 96% | 97% | 99% | 99% | 96% | 97% |
| Lycopene residual rate (after 4 months at 40° C.) | 98% | 99% | 96% | 97% | 97% | 97% | 94% | 96% |
| AUC (ng * 8 h/ml) | 2850 | 2860 | 2800 | — | 2910 | 2910 | 2810 | 580 |

|  | Comparative Example 2 | Comparative Example 3 | Comparative Example 4 | Comparative Example 5 | Comparative Example 6 | Comparative Example 7 |
|---|---|---|---|---|---|---|
| DSC absorption peak temperature | none | 153° C. | 152° C. | none | none | 153° C. |
| Observation by polarizing microscope | A | C | C | A | A | C |
| Lycopene residual rate (just after preparation) | 10% | 97% | 96% | 76% | 23% | 100% |
| Lycopene residual rate (after 4 months at 40° C.) | 8% | 80% | 79% | 62% | 14% | 76% |
| AUC (ng * 8 h/ml) | 2380 | 2660 | 720 | — | — | 590 |

As listed in Tables 1 and 2, the oil phase compositions of Example 1 to Example 7 were compositions, in which no application, or technical standard was specifically and individually indicated as being incorporated by reference.

The invention claimed is:

1. A carotenoid-containing, oil-in-water emulsified composition, comprising:
   a carotenoid component comprising at least one crystalline carotenoid, at least 90% by mass of the crystalline carotenoid being non-crystalline;
   a (poly)glycerol fatty acid ester having from 1 to 6 glycerin units and from 1 to 6 fatty acid units and having at least one hydroxyl group from a glycerin unit; and
   at least one phenolic antioxidant selected from the group consisting of aromatic carboxylic acids, cinnamic acids, and ellagic acids,
   wherein:
   the composition is oil-in-water emulsified;
   the crystalline carotenoid is lycopene; and
   the (poly)glycerol fatty acid ester has a hydrophilicity-hydrophobicity balance designated by the acronym HLB of 6 or less.

2. The carotenoid-containing, oil-in-water emulsified composition according to claim 1, wherein the phenolic antioxidant is a cinnamon acid.

3. The carotenoid-containing, oil-in-water emulsified composition according to claim 1, wherein the phenolic antioxidant is a cinnamon acid; and the cinnamon acid is at least one selected from the group consisting of ferulic acid, γ-orizanol, caffeic acid and chlorogenic acid.

4. The carotenoid-containing, oil-in-water emulsified composition according to claim 1, further comprising an ascorbic acid-based antioxidant as another antioxidant.

5. The carotenoid-containing, oil-in-water emulsified composition according to claim 1, wherein the molecular weight of the (poly)glycerol fatty acid ester is 10000 or less.

6. The carotenoid-containing, oil-in-water emulsified composition according to claim 1, wherein the total mass of the (poly)glycerol fatty acid ester is from 0.01 times to 10 times the total mass of the crystalline carotenoid.

7. The carotenoid-containing, oil-in-water emulsified composition according to claim 1, wherein the total content of the phenolic antioxidant in the composition is from 1.3 times to 15.0 times the content of the carotenoid component by molar ratio.

8. The carotenoid-containing, oil-in-water emulsified composition according to claim 1, further comprising an ascorbic acid-based antioxidant as another antioxidant, wherein the total content of the ascorbic acid-based antioxidant in the composition is from 0.6 times to 7.0 times the content of the carotenoid component by molar ratio.

9. The carotenoid-containing, oil-in-water emulsified composition according to claim 1, wherein each fatty acid of the fatty acid units of the (poly)glycerol fatty acid ester is a fatty acid having a carbon number of from 8 to 22.

10. A method for producing the carotenoid-containing, oil-in-water emulsified composition according to claim 1, the method comprising:
    preparing an oil phase component mixed liquid including the carotenoid component, the (poly)glycerol fatty acid ester and the phenolic antioxidant; and
    heating the oil phase component mixed liquid under a condition of a temperature of not less than a dissolution temperature of the carotenoid component.

11. The production method according to claim 10, wherein a difference between a maximum temperature during the heating and the dissolution temperature of the carotenoid component is 15° C. or less.

12. The production method according to claim 10, further comprising mixing an oil phase composition obtained from an oil phase component heating process with an aqueous phase composition including an aqueous phase component and performing emulsification.

13. The carotenoid-containing, oil-in-water emulsified composition according to claim 1, wherein the (poly)glycerol fatty acid ester is selected from the group consisting of glyceryl myristate, glyceryl monostearate, diglyceryl monostearate, tetraglyceryl pentastearate, and hexaglyceryl pentastearate.

* * * * *